(12) United States Patent
Librot

(10) Patent No.: US 10,433,921 B2
(45) Date of Patent: Oct. 8, 2019

(54) APPARATUS AND METHODS FOR ROBOT ASSISTED BONE TREATMENT

(71) Applicant: Mako Surgical Corp., Fort Lauderdale, FL (US)

(72) Inventor: Dan Librot, Westwood, NJ (US)

(73) Assignee: Mako Surgical Corp., Fort Lauderdale, FL (US)

( * ) Notice: Subject to any disclaimer, the term of this patent is extended or adjusted under 35 U.S.C. 154(b) by 431 days.

(21) Appl. No.: 15/383,303

(22) Filed: Dec. 19, 2016

(65) Prior Publication Data

US 2017/0181755 A1     Jun. 29, 2017

Related U.S. Application Data

(60) Provisional application No. 62/271,599, filed on Dec. 28, 2015.

(51) Int. Cl.
| | | |
|---|---|---|
| *A61B 34/30* | (2016.01) | |
| *A61B 34/10* | (2016.01) | |
| *A61B 34/20* | (2016.01) | |
| *A61B 17/56* | (2006.01) | |
| *A61B 90/00* | (2016.01) | |

(52) U.S. Cl.
CPC .............. *A61B 34/30* (2016.02); *A61B 34/10* (2016.02); *A61B 34/20* (2016.02); *A61B 2017/564* (2013.01); *A61B 2034/102* (2016.02); *A61B 2034/105* (2016.02); *A61B 2034/108* (2016.02); *A61B 2034/2055* (2016.02); *A61B 2090/363* (2016.02)

(58) Field of Classification Search
CPC . A61B 17/88; A61B 17/8802; A61B 17/8805; A61B 17/8822; A61B 17/8825; A61B 17/883; A61B 17/8833; A61B 17/8836; A61B 34/10; A61B 34/20; A61B 34/30; A61B 2034/107; A61B 2034/108; A61B 2034/2046; A61B 2034/2055; A61B 2034/2057
See application file for complete search history.

(56) References Cited

U.S. PATENT DOCUMENTS

| | | | |
|---|---|---|---|
| 5,598,005 A * | 1/1997 | Wang ................. | A61B 17/8836 250/458.1 |
| 5,824,084 A | 10/1998 | Muschler | |
| 6,112,109 A | 8/2000 | D'Urso | |
| 6,319,712 B1 * | 11/2001 | Meenen ............. | A61F 2/30756 435/395 |
| 6,711,432 B1 | 3/2004 | Krause et al. | |

(Continued)

FOREIGN PATENT DOCUMENTS

WO      2014145406 A1    9/2014

*Primary Examiner* — Eric S Gibson
(74) *Attorney, Agent, or Firm* — Lerner, David, Littenberg, Krumholz & Mentlik, LLP

(57) ABSTRACT

A method for performing a surgical procedure includes planning a resection of a bone of a patient. A volume of the bone is removed according to the planned resection using a surgical tool. As the bone is removed, data corresponding to a shape and volume of the removed bone is tracked with a computer system operatively coupled to the surgical tool. A prosthesis is implanted onto the bone of the patient based on the tracked data corresponding to the shape of the removed bone.

19 Claims, 12 Drawing Sheets

(56) References Cited

U.S. PATENT DOCUMENTS

| | | | |
|---|---|---|---|
| 6,723,131 B2* | 4/2004 | Muschler | A61F 2/4644 623/23.51 |
| 7,747,311 B2* | 6/2010 | Quaid, III | A61B 17/3403 600/424 |
| 7,831,292 B2* | 11/2010 | Quaid | G06F 3/0346 600/424 |
| 8,095,200 B2* | 1/2012 | Quaid, III | A61B 17/3403 600/407 |
| 8,183,042 B2 | 5/2012 | Liao et al. | |
| 8,287,522 B2* | 10/2012 | Moses | A61B 17/1764 606/1 |
| 8,391,954 B2* | 3/2013 | Quaid, III | A61B 17/3403 600/424 |
| 8,483,863 B1 | 7/2013 | Knox | |
| 8,551,178 B2 | 10/2013 | Sharkey et al. | |
| 8,617,171 B2 | 12/2013 | Park et al. | |
| 8,652,148 B2* | 2/2014 | Zuhars | A61F 2/30756 600/426 |
| 8,657,482 B2 | 2/2014 | Malackowski et al. | |
| 8,845,736 B2 | 9/2014 | Zhang et al. | |
| 8,911,499 B2* | 12/2014 | Quaid | G06F 19/00 623/18.11 |
| 9,002,426 B2* | 4/2015 | Quaid | G06F 19/00 600/407 |
| 9,039,998 B2 | 5/2015 | Guillemot et al. | |
| 9,056,017 B2 | 6/2015 | Kotlus | |
| 9,060,794 B2* | 6/2015 | Kang | A61B 17/1622 |
| 9,492,237 B2* | 11/2016 | Kang | A61B 17/1764 |
| 9,636,185 B2* | 5/2017 | Quaid | G06F 19/00 |
| 9,724,165 B2* | 8/2017 | Arata | A61B 17/1764 |
| 9,775,681 B2* | 10/2017 | Quaid | G06F 19/00 |
| 9,775,682 B2* | 10/2017 | Quaid | G06F 19/00 |
| 10,028,789 B2* | 7/2018 | Quaid | A61B 17/1764 |
| 10,085,804 B2* | 10/2018 | Nortman | A61F 2/30771 |
| 10,231,790 B2* | 3/2019 | Quaid | G06F 19/00 |
| 2005/0272153 A1 | 12/2005 | Xuenong et al. | |
| 2006/0142657 A1* | 6/2006 | Quaid | G06F 19/00 600/424 |
| 2007/0142751 A1* | 6/2007 | Kang | G06F 19/00 600/587 |
| 2007/0173815 A1* | 7/2007 | Murase | A61B 17/15 606/53 |
| 2007/0265705 A1 | 11/2007 | Gaissmaier et al. | |
| 2007/0270685 A1* | 11/2007 | Kang | A61B 17/1764 600/424 |
| 2008/0004633 A1* | 1/2008 | Arata | A61B 17/1764 606/130 |
| 2008/0010705 A1* | 1/2008 | Quaid | A61B 17/1764 600/407 |
| 2008/0010706 A1* | 1/2008 | Moses | A61B 17/1764 600/407 |
| 2009/0000626 A1* | 1/2009 | Quaid | G06F 19/00 128/898 |
| 2009/0000627 A1* | 1/2009 | Quaid | G06F 19/00 128/898 |
| 2009/0012531 A1* | 1/2009 | Quaid | G06F 19/00 606/130 |
| 2009/0012532 A1* | 1/2009 | Quaid | G06F 19/00 606/130 |
| 2009/0306499 A1* | 12/2009 | Van Vorhis | A61B 34/20 600/426 |
| 2009/0314925 A1* | 12/2009 | Van Vorhis | A61B 34/20 250/203.2 |
| 2010/0016467 A1* | 1/2010 | Truckai | A61B 17/8822 523/116 |
| 2010/0217400 A1* | 8/2010 | Nortman | A61F 2/30771 623/20.14 |
| 2010/0256504 A1* | 10/2010 | Moreau-Gaudry | A61B 5/0066 600/476 |
| 2010/0256692 A1* | 10/2010 | Kang | A61F 2/4644 606/86 R |
| 2011/0172611 A1 | 7/2011 | Yoo et al. | |
| 2012/0109152 A1* | 5/2012 | Quaid, III | A61B 17/3403 606/130 |
| 2013/0053648 A1* | 2/2013 | Abovitz | A61B 90/30 600/249 |
| 2013/0060278 A1* | 3/2013 | Bozung | A61B 17/32002 606/205 |
| 2013/0144392 A1 | 6/2013 | Hughes | |
| 2014/0180290 A1* | 6/2014 | Otto | A61B 17/1703 606/80 |
| 2014/0188134 A1* | 7/2014 | Nortman | A61F 2/30771 606/130 |
| 2014/0194887 A1* | 7/2014 | Shenoy | A61B 17/8811 606/94 |
| 2014/0263214 A1 | 9/2014 | Dahotre et al. | |
| 2014/0371897 A1 | 12/2014 | Lin et al. | |
| 2015/0182295 A1 | 7/2015 | Bozung et al. | |
| 2016/0338782 A1* | 11/2016 | Bowling | A61B 34/37 |
| 2017/0020613 A1* | 1/2017 | Kang | A61B 17/1764 |
| 2017/0151021 A1* | 6/2017 | Quaid, III | A61B 17/3403 |
| 2017/0181755 A1* | 6/2017 | Librot | A61B 34/10 |
| 2017/0333137 A1* | 11/2017 | Roessler | A61B 34/10 |
| 2017/0333138 A1* | 11/2017 | Arata | A61B 17/1764 |
| 2017/0340389 A1* | 11/2017 | Otto | A61B 34/10 |
| 2018/0168749 A1* | 6/2018 | Dozeman | A61B 34/30 |
| 2018/0168750 A1* | 6/2018 | Staunton | A61B 34/77 |
| 2019/0015164 A1* | 1/2019 | Quaid | A61B 17/1764 |
| 2019/0029764 A1* | 1/2019 | Nortman | A61F 2/30771 |

* cited by examiner

APPARATUS AND METHODS FOR ROBOT ASSISTED BONE TREATMENT

CROSS-REFERENCE TO RELATED APPLICATIONS

The present application claims the benefit of the filing date of U.S. Provisional Application No. 62/271,599, filed Dec. 28, 2015, the disclosure of which is hereby incorporated by reference herein.

BACKGROUND OF THE DISCLOSURE

The functions of a computer-assisted surgery (CAS) system may include pre-operative planning of a procedure, presenting pre-operative diagnostic information and images in useful formats, presenting status information about a procedure as it takes place, and enhancing performance. The CAS system may be used for procedures in traditional operating rooms, interventional radiology suites, mobile operating rooms or outpatient clinics.

Navigation systems may be used to display the positions of surgical tools with respect to preoperative or intraoperative image datasets. These images may include two-dimensional fluoroscopic images, and three-dimensional images generated using, for example, magnetic resonance imaging (MRI), computed tomography (CT) and positron emission tomography (PET). Some navigation systems make use of a tracking or localizing system. These systems locate markers attached or fixed to an object, such as an instrument or a patient, and track the position of markers. These tracking systems may be optical and/or magnetic, but may also include acoustic and/or ultrasonic systems. Optical systems may have a stationary stereo camera pair that observes passive reflective markers or active infrared LEDs attached to the tracked tools. Magnetic systems may have a stationary field generator that emits a magnetic field that is sensed by small coils integrated into the tracked tools.

Most navigation systems transmit information to the surgeon via a computer monitor. Conversely, the surgeon transmits information to the system via a keyboard and mouse, touchscreen, voice commands, control pendant, or foot pedals, and also by moving the tracked tool. The visual displays of navigation systems may display multiple slices through three-dimensional diagnostic image datasets.

Autonomous robots have been applied commercially to joint replacement procedures. These systems make precise bone resections, improving implant fit and placement relative to techniques that rely on manual instruments. Robots may also utilized haptic feedback systems to provide for semi-autonomous control, as described in greater detail below. Registration is performed by having the robot touch fiducial markers screwed into the bones or a series of points on the bone surfaces. Cutting is performed autonomously with a high-speed bur, although the surgeon can monitor progress and interrupt it if necessary. Bones may be clamped in place during registration and cutting, and are monitored for motion, which then requires re-registration.

Despite the advances in robotic devices and methods to perform or assist in the performance of certain surgeries, further advances are still desirable. For example, while robotic systems have been used to resect a patient's bone, it would be desirable to integrate the same robot into related procedures, such as in creating and/or applying a bone graft.

BRIEF SUMMARY OF THE INVENTION

According to a first embodiment of the disclosure, a method of performing a surgical procedure on a patient includes planning a resection of a bone of the patient, and removing a volume of the bone with a surgical tool according to the planned resection. Data corresponding to a shape and volume of the removed bone is tracked with a computer system operatively coupled to the surgical tool, and a prostheses is implanted onto the bone of the patient based on the tracked data corresponding to the shape and volume of the removed bone.

The surgical tool for removing the volume of the bone may be operatively coupled to a robotic device during the removal step. The surgical tool may be a manual tool. The implanted prosthesis may be deposited on the bone with a deposition tool operatively coupled to a robotic device during the implanting step. The deposition tool may be a syringe device. The implanted prosthesis may be an ultraviolet curable resin. A temperature of the prosthesis may be monitored during the implanting step.

The implanting step may further include forming a lattice on the resected bone with a first deposition tool containing a first prosthesis therein, with the first deposition tool being operatively coupled to a robotic device, and filling the lattice with a second prosthesis, which may contained in a second deposition tool operatively coupled to the robotic device.

The implanting step may further include implanting a first prosthesis layer on the resected bone with a first deposition tool operatively coupled to a robotic device, the first prosthesis layer having a first density, and implanting a second prosthesis layer on the first prosthesis layer, which may be done with a second deposition tool operatively coupled to a robotic device, the second prosthesis layer having a second density different than the first density. The second density may be greater than the first density.

The method may further include shaping the prosthesis using the surgical tool so that the prosthesis has a shape complementary to the shape of the removed bone. The surgical tool may be selected from one of the group consisting of a bur, saw, laser, cautery device, and waterjet. During the step of shaping the prosthesis, the prosthesis may be secured to a holding device. The step of removing the volume of the bone may include forming a first geometric shape in the bone and the step of shaping the prosthesis includes forming a second geometric shape in the prosthesis, the first geometric shape being keyed to the second geometric shape. The first and second geometric shapes may form a dovetail configuration. The step of implanting the prosthesis onto the bone of the patient may include coupling the prosthesis onto the bone with a fastener. The fastener may be selected from the group consisting of bone screws and bone pins. A feature for accepting the fastener may be formed into at least one of the bone and the prosthesis. The feature may be selected from one of the group consisting of a threaded screw hole and pilot hole. The step of shaping the prosthesis using the surgical tool may include forming a plurality of discrete prostheses, and the step of implanting the prosthesis onto the bone may include implanting each of the discrete prostheses.

DETAILED DESCRIPTION

Figure 1:
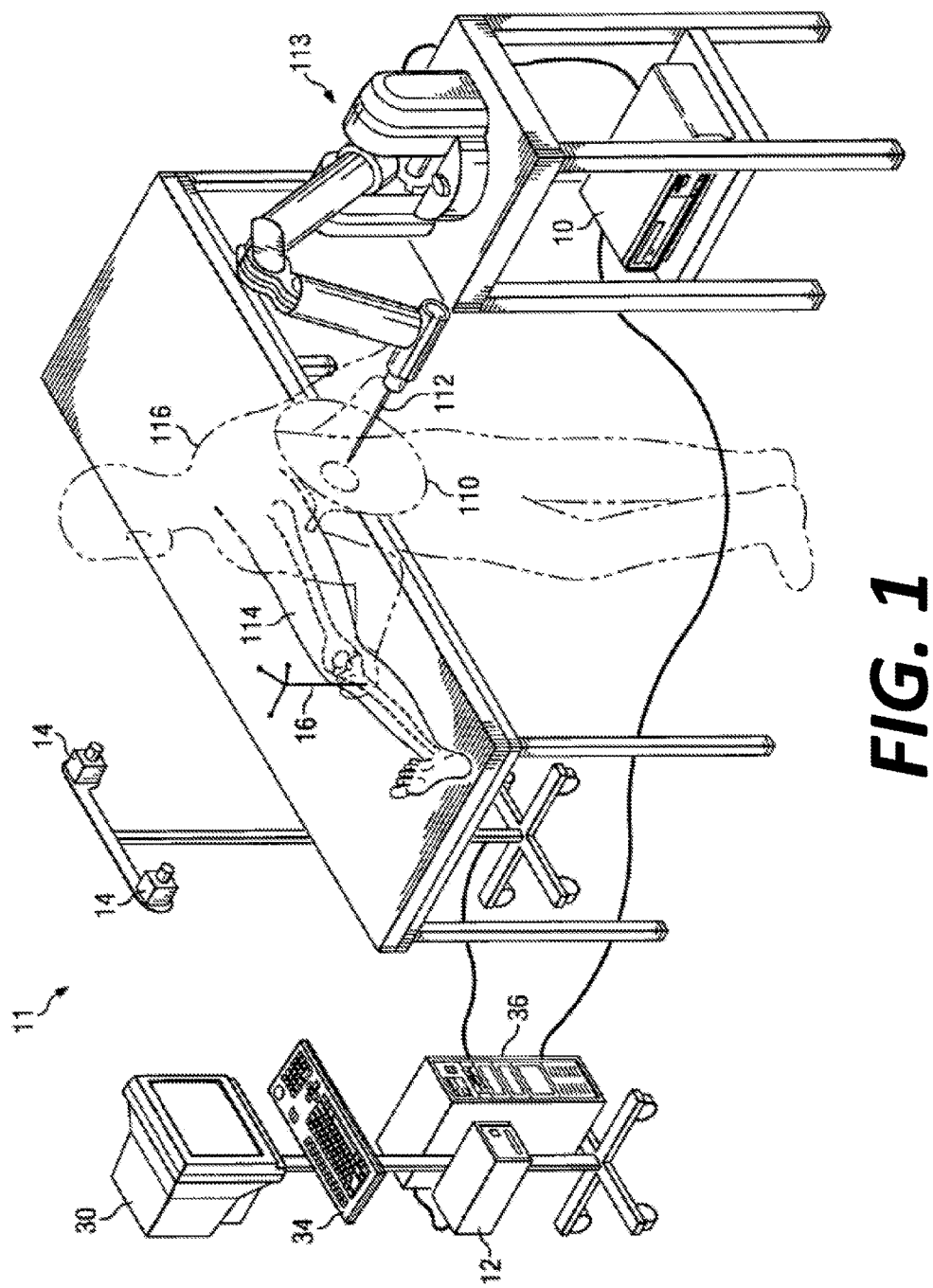
FIG. 1 is a diagrammatic illustration of an exemplary operating room in which a haptic device is used with a computer-assisted surgery system.

FIG. 1 is a diagrammatic illustration of an exemplary operating room in which a haptic device 113 is used with a computer-assisted surgery system 11. Computer-assisted surgery system 11 may include a display device 30, an input device 34, and a processor based system 36, for example a computer. Input device 34 may be any suitable input device including, for example, a keyboard, a mouse, or a touch screen. Display device 30 may be any suitable device for displaying two-dimensional and/or three-dimensional images, for example a monitor or a projector. If desired, display device 30 may be a touch screen and be used as an input device. One example of a system incorporating a haptic device 113 is described in greater detail in U.S. Pat. No. 7,831,292, the entire disclosure of which is hereby incorporated by reference herein.

Haptic device 113 is, in the illustrated example, a robotic device. Haptic device 113 may be controlled by a processor based system, for example a computer 10. Computer 10 may also include power amplification and input/output hardware. Haptic device 113 may communicate with computer-assisted surgery system 11 by any suitable communication mechanism, whether wired or wireless.

Also shown in FIG. 1 is a storage medium 12 coupled to processor based system 36. Storage medium 12 may accept a digital medium which stores software and/or other data. A surgical tool or instrument 112 is shown coupled to haptic device 113. Surgical tool 112 is preferably mechanically coupled to haptic device 113, such as by attaching or fastening it. However, if desired, surgical tool 112 may be coupled, either directly or indirectly, to haptic device 113 by any other suitable method, for example magnetically. Surgical tool 112 may be haptically controlled by a surgeon remotely or haptically controlled by a surgeon 116 present in proximity to surgical tool 112, although autonomous control with surgeon oversight is possible as well. Surgical tool 112 may be, for example, a bur, saw, laser, waterjet, cautery tool, or other trackable tool capable of cutting or otherwise shaping or resecting patent tissue, including bone. Patient tissue and bone may be referred to interchangeably herein and may include cartilage, tendons, skin tissue, and/or bone whether it be cortical or cancellous bone.

Haptic object 110 is a virtual object used to guide and/or constrain the movement and operations of surgical tool 112 to a target area inside a patient's anatomy 114, for example the patient's leg. In this example, haptic object 110 is used to aid the surgeon 116 to target and approach the intended anatomical site of the patient. Haptic feedback forces may be used to slow and/or stop the surgical tool's movement if it is detected that a portion of surgical tool 112 will intrude or cross over pre-defined boundaries of the haptic object. Furthermore, haptic feedback forces can also be used to attract (or repulse) surgical tool 112 toward (or away from) haptic object 110 and to (or away from) the target. If desired, surgeon 116 may be presented with a representation of the anatomy being operated on and/or a virtual representation of surgical tool 112 and/or haptic object 110 on display 30.

The computer-assisted surgery ("CAS") system preferably includes a localization or tracking system that determines or tracks the position and/or orientation of various trackable objects, such as surgical instruments, tools, haptic devices, patients, donor tissue and/or the like. The tracking system may continuously determine, or track, the position of one or more trackable markers disposed on, incorporated into, or inherently a part of the trackable objects, with respect to a three-dimensional coordinate frame of reference. Markers can take several forms, including those that can be located using optical (or visual), magnetic or acoustical methods. Furthermore, at least in the case of optical or visual systems, location of an object's position may be based on intrinsic features, landmarks, shape, color, or other visual appearances, that, in effect, function as recognizable markers.

Any type of tracking system may be used, including optical, magnetic, and/or acoustic systems, which may or may not rely on markers. Many tracking systems are typically optical, functioning primarily in the infrared range. They may include a stationary stereo camera pair that is focused around the area of interest and sensitive to infrared radiation. Markers emit infrared radiation, either actively or passively. An example of an active marker is a light emitting diode (LED). An example of a passive marker is a reflective marker, such as ball-shaped marker with a surface that reflects incident infrared radiation. Passive systems may include an infrared radiation source to illuminate the area of focus. A magnetic system may have a stationary field generator that emits a magnetic field that is sensed by small coils integrated into the tracked tools.

With information from the tracking system on the location of the trackable markers, CAS system 11 may be programmed to be able to determine the three-dimensional coordinates of an end point or tip of a tool and, optionally, its primary axis using predefined or known (e.g. from calibration) geometrical relationships between trackable markers on the tool and the end point and/or axis of the tool. A patient, or portions of the patient's anatomy, can also be tracked by attachment of arrays of trackable markers. In the illustrated example, the localizer is an optical tracking system that comprises one or more cameras 14 that preferably track a probe 16. As shown in FIG. 1, cameras 14 may be coupled to processor based system 36. If desired, cameras 14 may be coupled to computer 10. Probe 16 may be a conventional probe. If desired, the probe may be rigidly attached to haptic device 113 or integrated into the design of haptic device 113.

In one implementation, processor based system 36 may include image guided surgery software to provide certain user functionality, e.g., retrieval of previously saved surgical information, preoperative surgical planning, determining the position of the tip and axis of instruments, registering a patient and preoperative and/or intraoperative diagnostic image datasets to the coordinate system of the tracking system, etc. Full user functionality may be enabled by providing the proper digital medium to storage medium 12 coupled to computer 36. The digital medium may include an application specific software module. The digital medium may also include descriptive information concerning the surgical tools and other accessories. The application specific software module may be used to assist a surgeon with planning and/or navigation during specific types of procedures. For example, the software module may display predefined pages or images corresponding to specific steps or stages of a surgical procedure. At a particular stage or part of a module, a surgeon may be automatically prompted to perform certain tasks or to define or enter specific data that will permit, for example, the module to determine and display appropriate placement and alignment of instrumentation or implants or provide feedback to the surgeon. Other pages may be set up to display diagnostic images for navigation and to provide certain data that is calculated by the system for feedback to the surgeon. Instead of or in addition to using visual means, the CAS system could also communicate information in other ways, including audibly (e.g. using voice synthesis) and tactilely, such as by using a haptic interface. For example, in addition to indicating visually a trajectory for a drill or saw on the screen, a CAS system may feed information back to a surgeon whether he is nearing some object or is on course with an audible sound. To further reduce the burden on the surgeon, the module may automatically detect the stage of the procedure by recognizing the instrument picked up by a surgeon and move immediately to the part of the program in which that tool is used.

The software which resides on computer 36, alone or in conjunction with the software on the digital medium, may process electronic medical diagnostic images, register the acquired images to the patient's anatomy, and/or register the acquired images to any other acquired imaging modalities, e.g., fluoroscopy to CT, MRI, etc. If desired, the image datasets may be time variant, i.e. image datasets taken at different times may be used. Media storing the software module can be sold bundled with disposable instruments specifically intended for the procedure. Thus, the software module need not be distributed with the CAS system. Furthermore, the software module can be designed to work with specific tools and implants and distributed with those tools and implants. Moreover, CAS system can be used in some procedures without the diagnostic image datasets, with only the patient being registered. Thus, the CAS system need not support the use of diagnostic images in some applications i.e. an imageless application.

Haptic device 113 may be used in combination with the tracking and imaging systems described above to perform highly accurate bone resections and grafting bone on the resected bone. A general description of such a procedure is described below, followed by at least two particular examples of the procedure.

Figure 2:
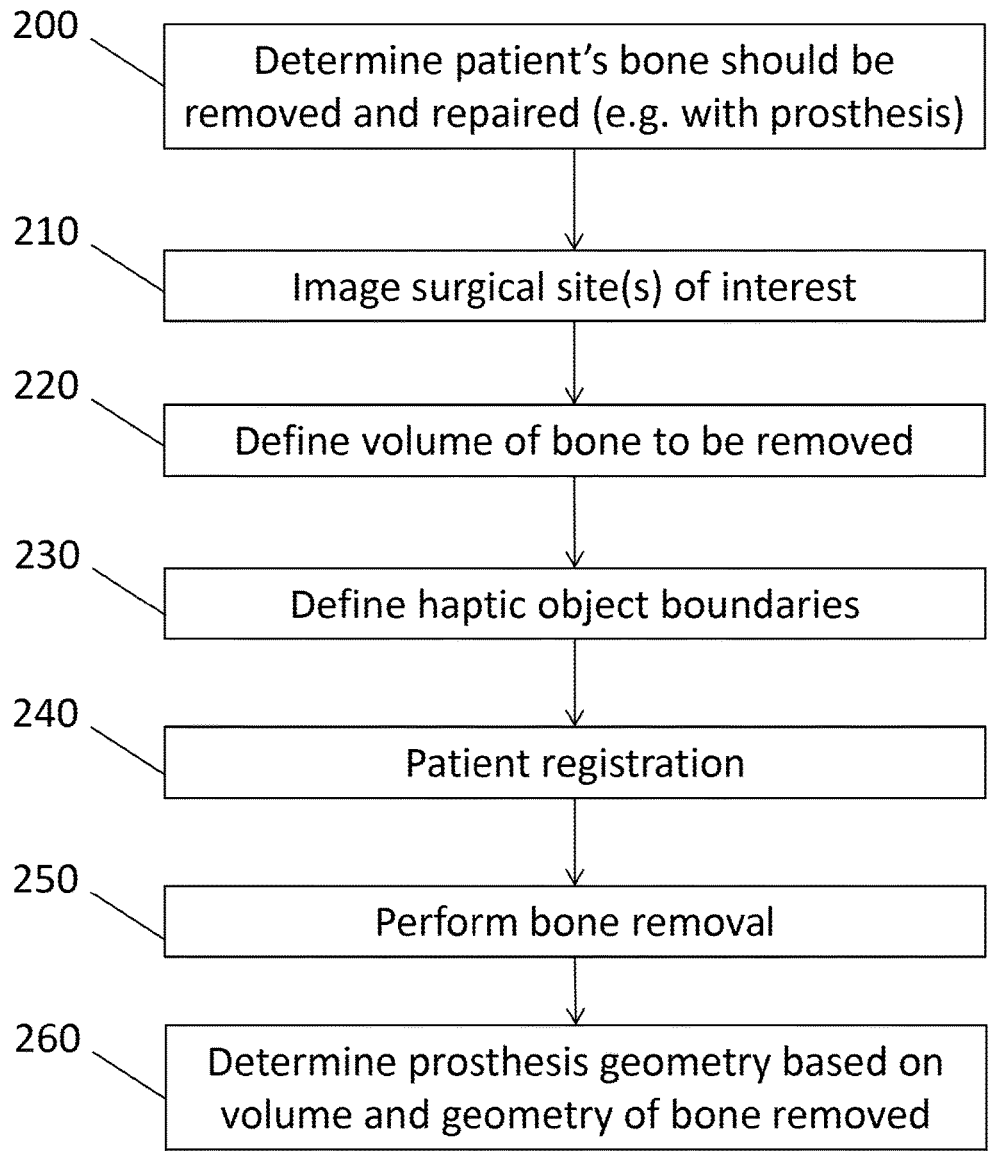
FIG. 2 is a flowchart of a surgical method according to one aspect of the disclosure.

FIG. 2 illustrates a flow chart of a surgical procedure according to the present disclosure. In a first step 200, a physician or other medical practitioner diagnoses that a patient would benefit from having a portion of a bone removed or resected followed by implantation of a prosthesis onto the bone at or near the site of resection. In this regard, the term prosthesis encompasses transplanted bone including, for example, allograft, autograft, xenograft, or bone substitute as well as other biologics, metals, plastics, and combinations thereof. After determining the intended surgical site, the surgical site may be imaged in step 210, for example via an MRI or CT scan, or any other suitable imaging modality. The images may be uploaded or otherwise transferred to processor based system 36 for use on the software residing therein. Three-dimensional models of individual bones and/or joints may be created from the images taken of the surgical site. Systems and method for image segmentation in generating computer models of a joint to undergo arthroplasty is disclosed in U.S. Pat. No. 8,617,171, the entire disclosure of which is hereby incorporated by reference herein. The images may be processed or otherwise used in order to plan portions of the surgical procedure in step 220. In one example, the desired geometry and/or volume of the bone to be removed or resected may be defined based on the images. The surgeon may define the geometry and/or volume using the software with manual definition or semi-automatic definition. For example, the surgeon may outline geometric boundaries on the images on display 30 with input device 34, such as a mouse, to determine the geometry and/or volume of bone to be removed. In addition or alternatively, the software may employ image processing to identify damaged areas of the bone, for example by determining bone quality, for example by analyzing bone density based on brightness or other parameters of the image, to provide for a suggested geometry and/or volume of bone removal which may be confirmed or altered by the surgeon. It should be understood that this geometry and/or volume definition step 220 may be performed prior to the surgical procedure on a separate computer system, with the results of this step imported to processor based system 36. It should also be understood that the steps shown in FIG. 2 do not necessarily need to be completed in the order shown. For example, a patient may be first imaged in step 210, and based on the results and analysis of the imaging, the determination that surgical intervention is required in step 200 may be made.

In step 230, the surgeon may define the boundaries of haptic object 110. This may be accomplished in one of several ways. In one example, the haptic object 110 may be based on the geometry and/or volume of bone to be removed determined in step 220. The haptic object 110 may be defined to have boundaries along the geometry and/or volume of bone to be removed so that the surgical tool 112, as described above, may aid the surgeon 116 to target and approach the intended anatomical site of the patient with surgical tool 112. In another example, a number of pre-defined shapes or volumes may be pre-loaded into computer 10 and/or computer 36. For example, different procedures may have certain typical shapes or volumes of intended bone removal, and one or more pre-loaded geometries and/or volumes may be included in the software application on computer 10 and/or computer 36, for example with each geometry and/or volume corresponding to one or more types of procedures. These pre-loaded shapes or volumes may be used without modification, but in many cases the pre-loaded geometries and/or volumes will be modified by the surgeon and/or combined with other pre-loaded geometries and/or volumes to meet the needs of the particular patient.

In step 240, haptic device 113 is registered to the anatomy of the patient. If desired, a representation of the anatomy of the patient displayed on display device 30 may also be registered with the anatomy of the patient so that information in diagnostic or planning datasets may be correlated to locations in physical space. For example, the haptic device 113 (or a probe attached thereto) may be directed to touch fiducial markers screwed into the bones, to touch a series of points on the bone to define a surface, and/or to touch anatomical landmarks. The registration step 240 is preferably performed when the anatomy is clamped or otherwise secured from undesired movement. Registration may also be performed using, for example, intraoperative imaging systems. However, the anatomy does not need to be clamped in certain situations, for example if tracking devices are coupled to the anatomy. In that case, any movement of the anatomy is tracked so that rigid fixation is not necessary.

In step 250, with patient registration complete, the bone removal procedure is performed. The procedure may be any suitable procedure in which bone is to be removed, such as resection in preparation for joint replacement, bulk bone removal, or small volume bone removal for treating small tumors or the like. The actual process of removing bone may be performed semi-autonomously under haptic control, as described above, autonomously by haptic device 113, manually via free-hand resection by the surgeon, or any combination of the above. Regardless of the specific procedure or the level of surgeon control, the bone removal geometry and/or volume is tracked by computer 10 (and/or computer 36) by tracking the position of surgical tool 112 with the navigation system and/or joint encoders of haptic device 113. Thus, even if the bone actually removed differs from the surgical plan, the computer 10 (and/or computer 36) tracks and stores information relating to the bone actually removed. In other embodiments, photo and/or pressure sensors may be employed with haptic device 113 to precisely measure the geometry and/or volume of bone that is removed. It is also contemplated that, following the bone removal, additional imaging may be performed and compared to patient images prior to the resection to determine bone actually removed, which may be used as an alternative to the robotic tracking of bone removal or as confirmation of same. Still further, instead of tracking and storing information to the bone actually removed during the removal process, the bone may first be removed, and following the bone removal, the remaining surface of the bone may be probed to register the precise remaining volume and/or geometry of bone.

With the information relating to the geometry and/or volume of bone removed from the patient, computer 10 and/or computer 36 determines the precise three-dimensional geometry of the prosthesis to be implanted into or onto the bone in step 260. Based on this determination, haptic device 113 may be used in any one of a number of ways to form and/or place the prosthesis. For example, if the prosthesis is an allograft bone, haptic device 113 may employ the determined geometry and/or volume to assist the surgeon in shaping the allograft bone to precisely fit the geometry of the resected bone. Alternately, a similar procedure may be used on the patient if the prosthesis is an autograft bone taken from another bone portion of the patient, with the haptic device 113 providing assistance to the surgeon in resecting the precise geometry and/or volume of autograft to replace the bone removed in step 250. In other embodiments, haptic device 113 may be employed to resect more autograft than will be needed to replace the bone removed in step 250 while taking into account whether such removal of autograft taken from the another bone portion of the patient is safe for the patient. Still further, a liquid or putty-type bone graft may be applied to the site of bone removal in step 250, for example by attaching a syringe-like device as the tool of haptic device 113, with precise application of the bone graft to the site of bone removal. Some of these examples are described in greater detail below.

As noted above, steps 200 through 260 do not necessarily need to be performed in the order shown in FIG. 2. For example, in some cases, it may be preferable to prepare the prosthesis prior to resecting the patient's bone. This may be true in the case of an autograft prosthesis since the donor tissue maybe limited and/or difficult to access. In such a case, the autograft may be prepared according to the surgeon's experience (manually or otherwise), the intended surgical procedure, and/or any pre- and intra-operative planning. Once the prosthesis is formed, the prosthesis may be probed and registered to using computer 10 and/or computer 36 so that the volume and/or geometry of the prosthesis is stored. The volume and/or geometry of the prosthesis may then be used to create the haptic object 110, so that the surgeon may use the haptic device 113 to resect the patient's bone to a shape corresponding to the geometry and/or volume of the previously prepared prosthesis.

Figure 3A:
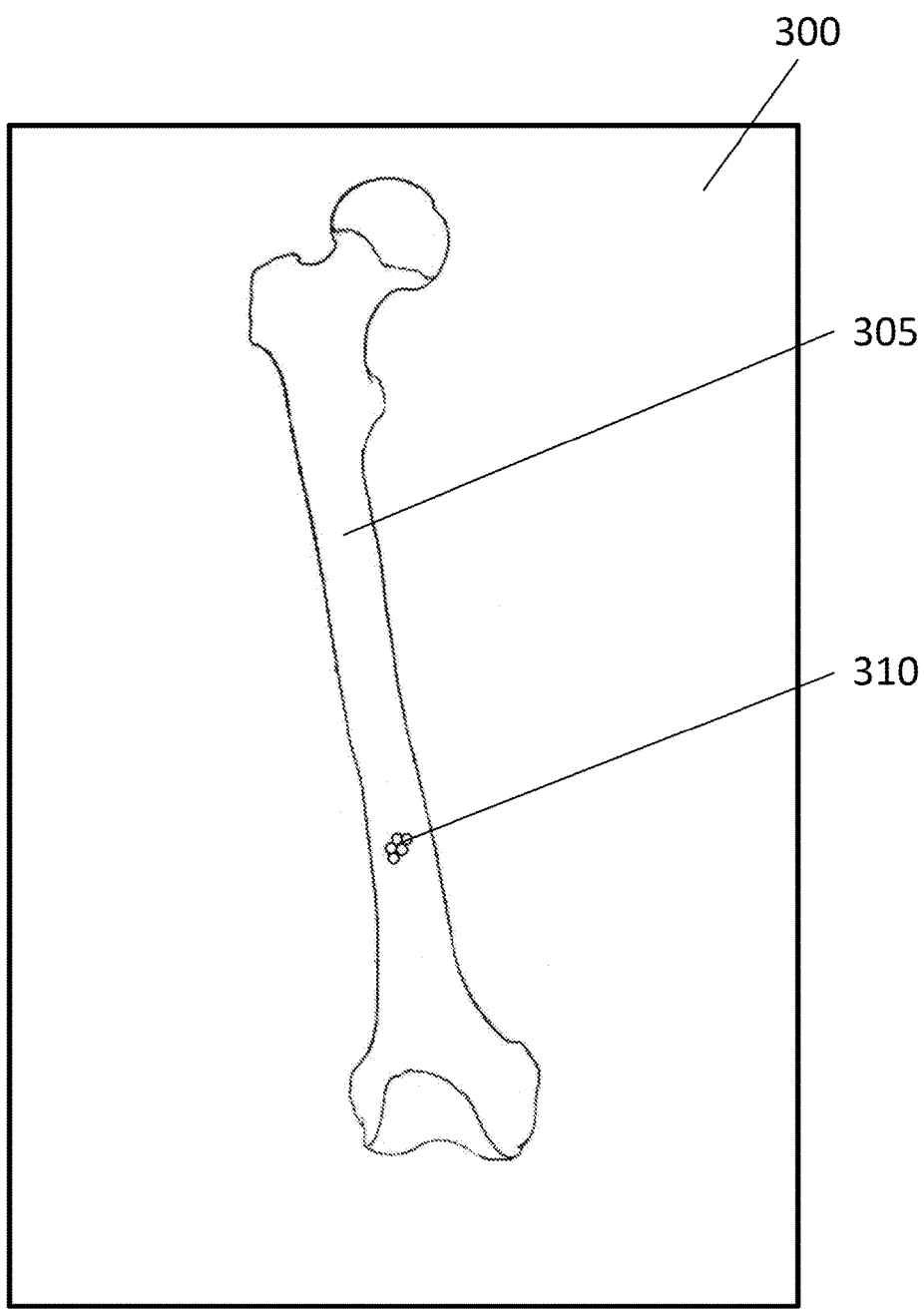
FIG. 3A illustrates an image of a bone to be treated by a surgical procedure according to one aspect of the disclosure.

One particular example of a procedure utilizing steps 200-260 of FIG. 2 is for treating interlesional bone tumors. Common types of such bone tumors that may be treated according to the below procedure may include giant cell tumors of bone, benign aneurysmal bone cysts, and malignant low grade chondrosarcomas. The patient's bone, including the tumor site, is imaged in step 210. A highly schematic illustration of an image 300 of a patient's femur 305 is shown in FIG. 3A with a bone tumor(s) 310 shown on the image. The image 300, or a set of images 300, may be uploaded or otherwise stored on processor-based system 36.

The processor-based system 36, for example with the aid of software, may automatically identify the location and/or boundaries of tumors(s) 310. In one example, this determination is based on bone density and/or quality information from the image 300. Tumor(s) 310 and surrounding portions of healthy femur 305 may have different density values, allowing for the correlation of image brightness to bone density in order to determine the boundaries between tumor(s) 310 and adjacent portions of healthy femur 305. The surgeon may review and confirm the determined location of tumor(s) 310, revise the determined location of the tumor(s), or otherwise manually identify the location of the tumor(s).

Figure 3B:
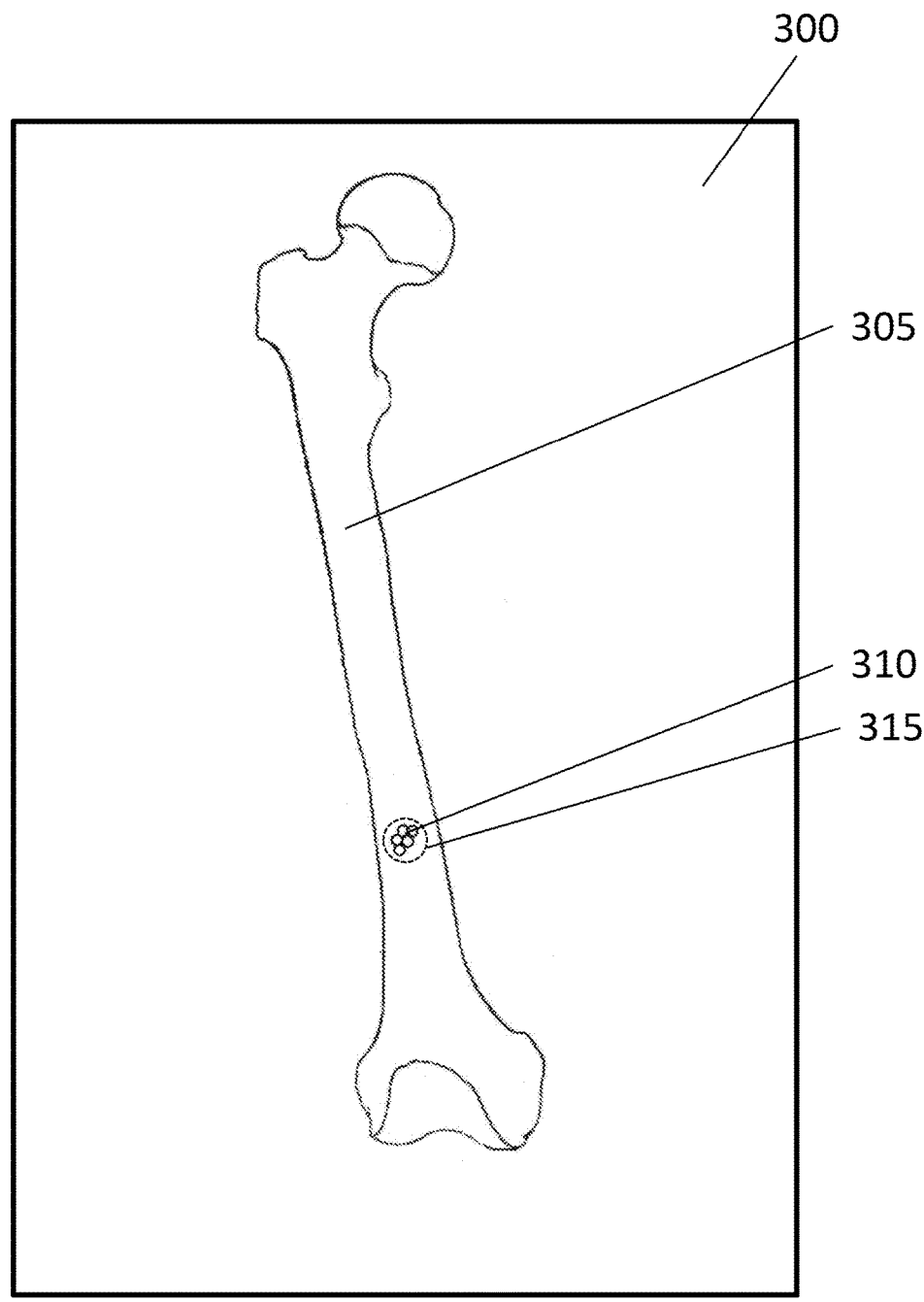
FIG. 3B illustrates an aspect of a surgical plan for the bone of FIG. 3A.

Based on the determination of the boundary between tumor(s) 310 and healthy femur 305, the processor-based system 36 may automatically determine the geometry and/or volume 315 of femur 305 to be resected to effectively remove tumor(s) 310, as provided by step 220 and as shown in FIG. 3B. In one example, the processor-based system 36 may apply a three-dimensional buffer around the determined boundary between tumor(s) 310 and healthy femur 305, for example a buffer of 0.5 mm, 1 mm, 2 mm, or 3 mm outside the boundary to help ensure that the removal of tumor(s) 310 is complete. In other examples, the software-based system 36 may provide a standard buffer, for example 1 mm, and the surgeon may confirm the buffer or revise the buffer. Still further, the surgeon may manually input the geometry and/or volume of bone to be removed, using his or her discretion regarding any appropriate buffer beyond the determined location of tumor(s) 310. Based on the geometry and/or volume 315 of bone to be removed, the system may determine a haptic object 110 correlating to the geometry and/or volume 315 as provided in step 230. As described in greater detail below, it is also contemplated that the surgeon may skip the step of defining the volume of bone to be removed, rather using his or her own experience to resect the bone to remove tumor(s) 310 using haptic device 113. As is described in greater detail below, the resection may alternately be a manual resection procedure.

Figure 3C:
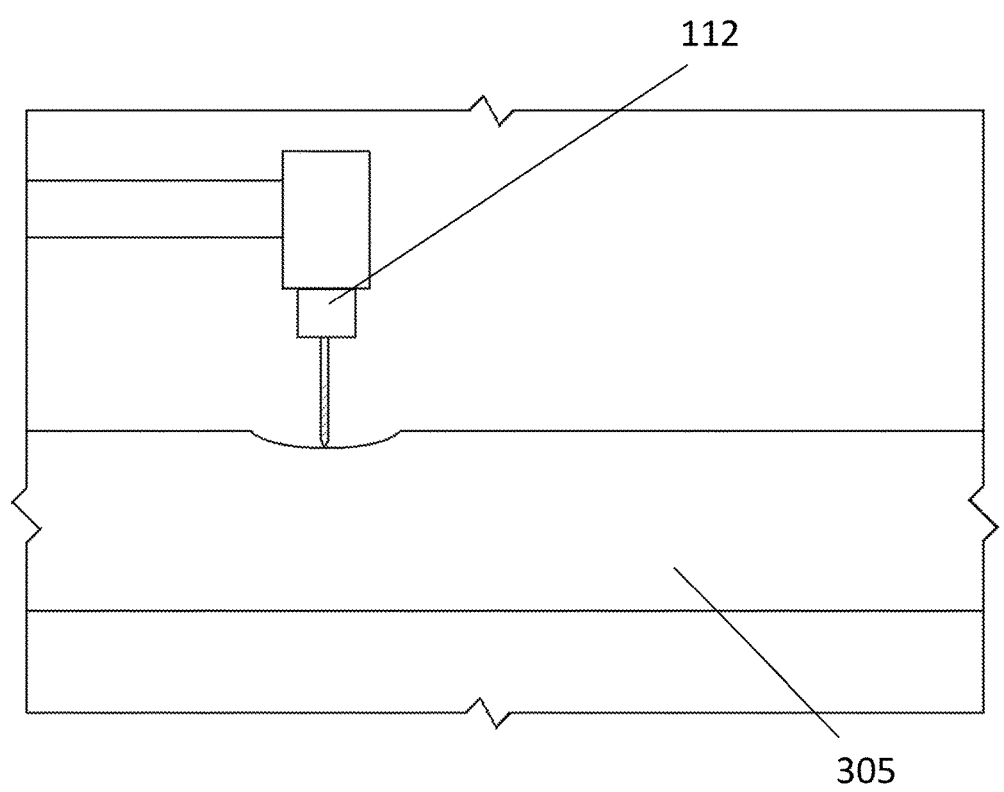
FIG. 3C is a highly schematic representation of the haptic device of FIG. 1 performing a resection on the bone of FIG. 3A.

Whether or not steps 220 and 230 are performed, the patient is then registered to the haptic device 113 as described above in connection with step 240. A surgical tool 112 in the form of a small bur may be coupled to haptic device 113 and used to remove the tumor(s) 310 on femur 305. If steps 220 and 230 were performed, the haptic device 113 may autonomously or semi-autonomously guide the bur using the constraints of the haptic object 110 to remove the desired geometry and/or volume 315 of bone, as shown in FIG. 3C. If steps 220 and 230 were not performed, the surgeon may manually guide the bur through manipulation of the haptic device 113. In either scenario, the path of the bur is tracked and information regarding the actual volume of bone removed is stored in computer 10 (and/or computer 36). Preferably, the tip and/or sides of the bur, or any relevant cutting surfaces, are tracked. It is further contemplated that, if steps 220 and 230 are not performed, a manual device, such as a curette, may be employed by the surgeon to remove the tumor(s) 310. The curette may be provided with a tracking array and be operatively coupled to computer 10 (and/or computer 36) so that the movements of the curette in space relative to the patient's bone are tracked, so that the precise volume of bone removed may be tracked for use in replacing the removed bone. For each example above, because the three-dimensional position of the patient's bone is known via registration and the image(s) 300, and the three-dimensional position of the surgical tool (e.g. bur or curette) is known via the tracking system, any time the tip of the surgical tool 112 intersects with the patient's bone, the portion of bone removed may be identified and stored by computer 10 (and/or computer 36).

In step 260, the precise geometry and/or volume of the prosthetic is determined. The prosthetic geometry and/or volume may be identical to that of the bone removed, as tracked during the removal step, whether the bone removal was autonomous, semi-autonomous, or manual. If the bone removal geometry and/or volume was pre-planned using computer 36, the geometry and/or volume of the prosthetic may be identical to the geometry and/or volume of the planned bone removal, since haptic device 113 helps ensure the bone removal occurs exactly (or nearly exactly) according to plan. Instead of forming the geometry of the prosthesis to be identical to the geometry and/or volume of the removed bone, modifications may be made, for example so that the prosthesis can have a press fit or interference fit with the patient's anatomy.

Figure 3D:
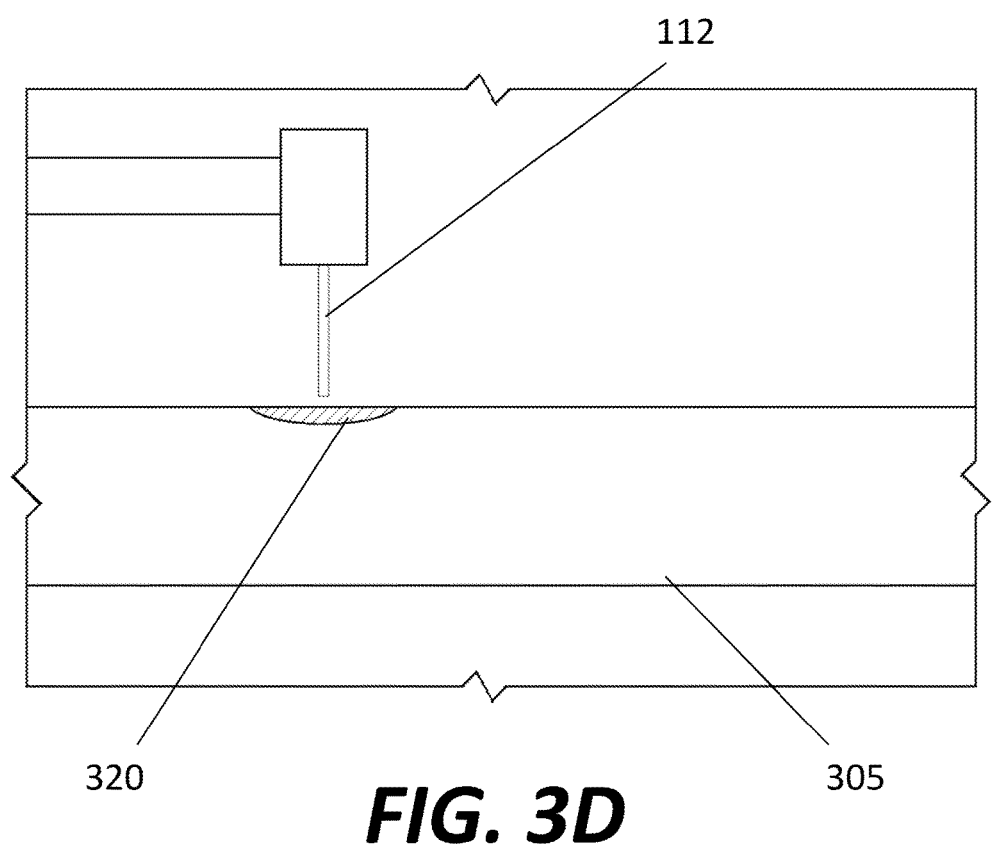
FIG. 3D is a highly schematic representation of the haptic device of FIG. 3C replacing the bone resected in FIG. 3A.

The prosthesis may take any suitable form, including, e.g., demineralized bone matrices ("DBM"), morselized autograft, morselized allograft, polymethyl methacrylate ("PMMA") bone cements, synthetic calcium phosphate or calcium sulfate based bone grafts, and/or ultraviolet ("UV") curable resins. If the prosthesis takes the form of one of the above void fillers, it may be delivered via syringe or syringe-like device. For example, as shown in FIG. 3D, the haptic device 113 may include a surgical tool 112 in the form of a syringe-like device packed with void filler 320. The void filler 320 may be ejected from the end effector 112 by haptic device 113 to precisely fill the volume of bone previously removed with the void filler 320. Alternately, the void filler 320 may be deposited in some other desired geometry and/or volume within the resected bone, such as a partial fill.

Rather than use a homogenous void filler 320, the process may be divided into steps to provide additional features of the prosthetic bone. For example, a surgical tool 112 with a syringe packed with a curable resin, such as a UV curable resin, may be coupled to haptic device 113. A curing source, such as a UV source, may be provided along with surgical tool 112 so that the curable resin cures contemporaneously or near-contemporaneously upon deposition into the bone void. A cured resin lattice may be formed in this manner, which may be then be infused with a void filler or a bone growth composition. The lattice may take the form of a structural three-dimensional matrix with voids that can be filled with a void filler and/or bone growth composition. This infusion may be accomplished by coupling a surgical tool 112 in the form of a syringe-like device packed with the bone growth material to haptic device 113, or manually by the surgeon.

Figure 3E:
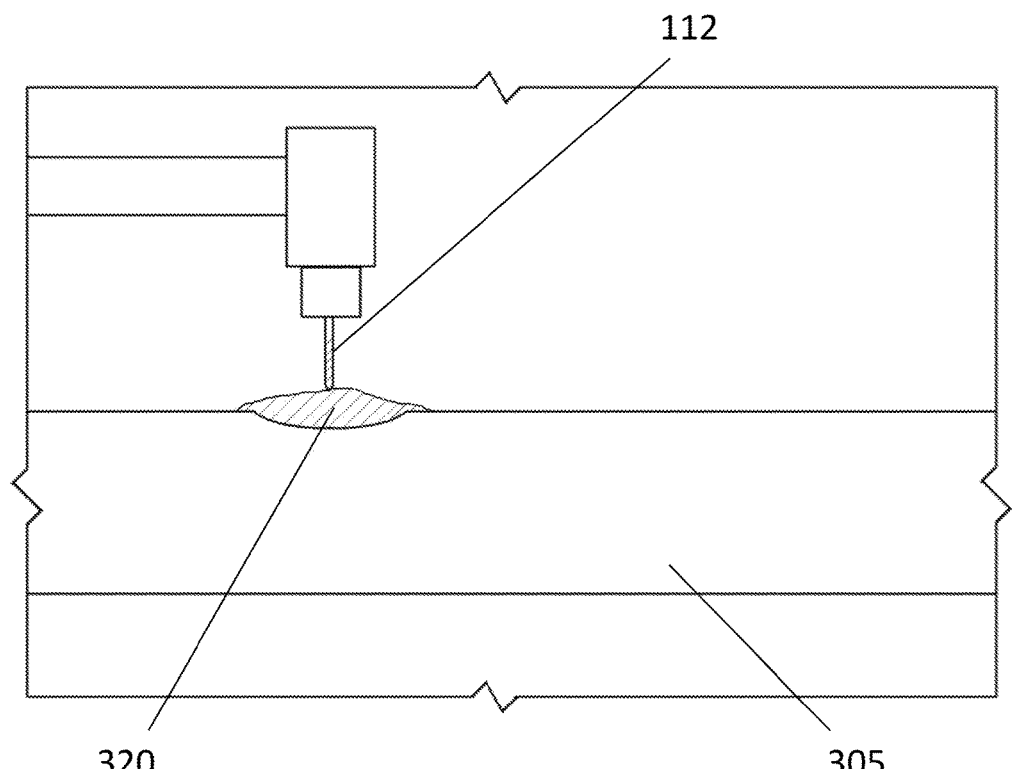
FIG. 3E is a highly schematic representation of the haptic device of FIG. 3C replacing the bone resected in FIG. 3A according to another aspect of the disclosure.

Another alternative, as shown in FIG. 3E, is to apply a large mass of void filler 320 into the void, for example manually, to partially or completely fill the void. If the void is completely filled with void filler 320, a bur or other surgical tool 112 is coupled to haptic device 113, and the haptic device 113 may autonomously or semi-autonomously cut away extraneous void filler 320 until the remaining void filler exactly matches the geometry and/or volume of resected bone.

With any of the void filler 320 deposition techniques described above, the void filler 320 may vary in quality in three-dimensions. For example, layers of filler 320 which have different densities may be applied as desired, for example by repeating the delivery described in connection with FIG. 3D in sequential steps using different fillers with different densities. This method may facilitate more closely mimicking the natural bone, for example where inner layers of cancellous bone are less dense than outer layers of cortical bone. Other ways to achieve variable prosthesis properties such as variable density include, for example, adding beads, mesh materials, or fibrous materials to the filler material. Still further, different layers may be deposited in an alternating fashion, such as a hard prosthesis having a liquid or filler material underneath and also on top of the hard prosthesis.

Some void fillers 320, such as bone cement, may be applied to the bone at a relatively high temperature and cure as the cement cools. The surgical tool 112 may incorporate a thermal sensor so that computer 10 (and/or computer 36) is able to detect a temperature of the void filler 320 packed into the effector. The computer 10 (and/or computer 36) may then control the deposition of the void filler 320 onto the bone so that the application occurs at an optimal viscosity and/or thermal optimum. For example, if the void filler 320 is too hot, the native bone may be damaged. However, if the void filler 320 is allowed to cool too much prior to deposition, the deposition may not be effective if the void filler 320 has already begun to harden.

Although the procedure above is described as tracking bone removal coincident with the bone removal process, other alternatives may be suitable. For example, after the bone removal is complete, a shapeable material may be pressed into the bone void to create a mold having a volume and/or geometry corresponding to the resected bone. It should be understood that this mold may actually be a "reverse" mold of the resected bone, since the mold has the shape of what was removed. The mold, once formed, may be removed from the bone and the surface probed and registered to determine the shape of the removed bone (and correspondingly the shape of the remaining bone).

Another example of a procedure utilizing steps 200-260 of FIG. 2 is for bulk allograft procedures, which may entail replacement of larger quantities of bone than a relatively minor bur or curettage procedure described above. It should be understood that, although the term allograft is used, the description may apply to autograft and/or xenograft procedures, unless explicitly described otherwise. Further, other types of prostheses, including metal and/or plastic procedures, may be used alternately to or in addition to tissue prostheses. Such bulk allograft procedures may include bone replacement after treating large tumors, treating trauma, or revisions of previously implanted prostheses, for example.

Structural bulk allograft procedures using tissue prostheses may provide certain benefits because the allograft may include soft tissue attachments to allow the surgeon to reconstruct the soft tissue with the promise of increased restoration of function. For example, a proximal tibial allograft may include a patellar tendon, a proximal femoral allograft may include hip abductor tendons, and a proximal humeral allograft may include rotator cuff tendons.

Figure 4A:
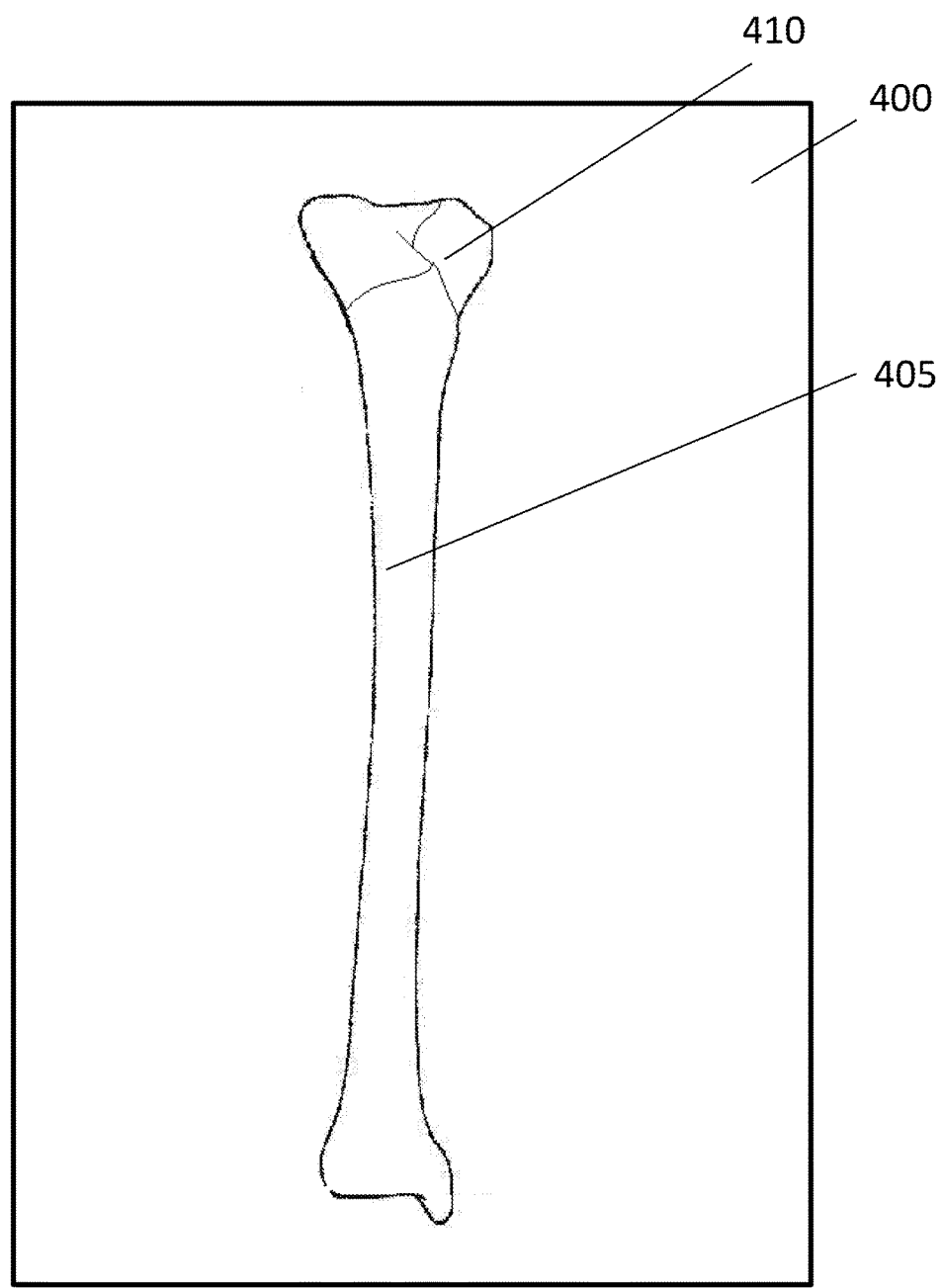
FIG. 4A illustrates an image of a bone to be treated by a surgical procedure according to an aspect of the disclosure.

As an example, a physician may determine that, following trauma to a proximal tibia, it would be beneficial to replace the proximal tibia with a bulk tissue allograft from a donor. The patient's bone, including the trauma site, is imaged in step 210. A schematic illustration of an image 400 of a patient's tibia 405 is shown in FIG. 4A with a tibial fracture 410 shown on the image. The image 400, or a set of images 400, may be uploaded or otherwise stored on processor based system 36.

Figure 4B:
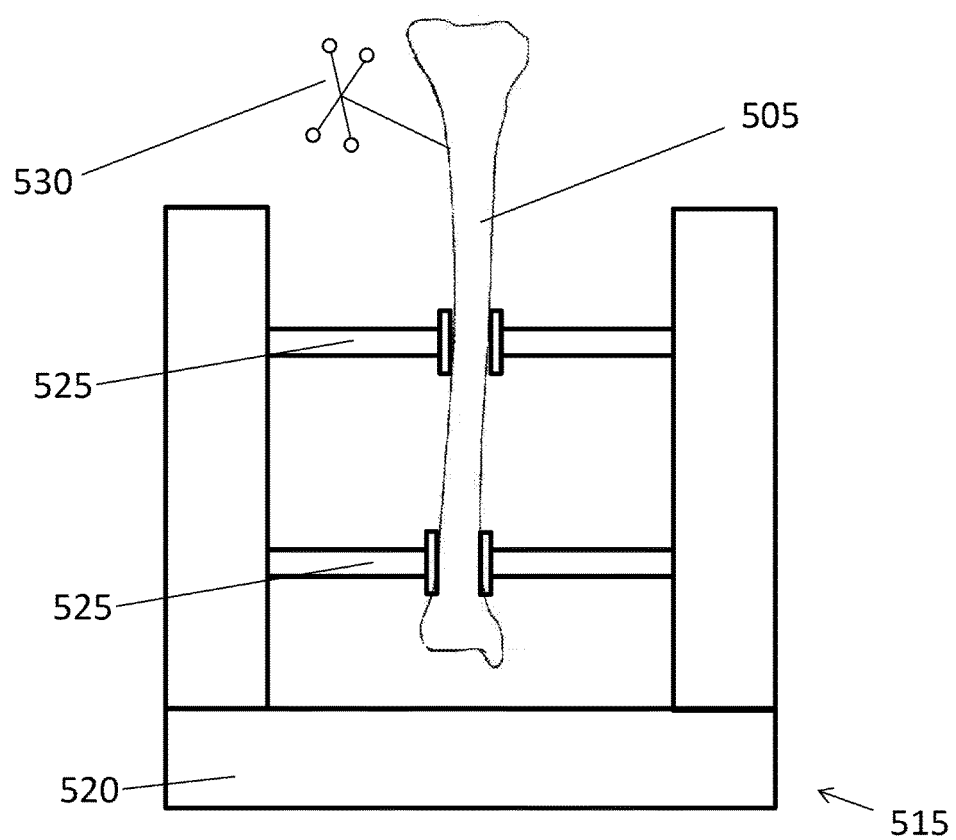
FIG. 4B illustrates a donor bone secured within a holding system for use in treatment of the bone of FIG. 4A.

An appropriate prosthesis, such as a donor tibia 505, may be secured into a holding device 515, as shown in FIG. 4B. In one example, the holding device 515 may include a base 520 and a plurality of clamps 525 to secure the donor tibia 505 in place. Holding device 515 may be a standalone device, may be attachable to an operating room accessory such as an operating table, a limb holder attached to the operating room table or the haptic device 113, or may be integrated with an operating room accessory such as an operating table or the haptic device 113. Instead or in addition to the holding device 515, the donor tibia 505 may have one or more trackers 530 attached so that movement of the donor tibia 505, intentional or not, is captured by the navigation system. The ability to use one or more trackers with the donor tibia 505 may apply with equal force to other implants described in this disclosure.

The donor tibia 505, including any soft tissue attachments, such as a patellar tendon, may be imaged if desired. In one example, imaging the donor tibia 505 and/or soft tissue attachments may provide information that may be useful to the surgeon in the procedure. For example, density information of the donor tibia 505 may be obtained from the image and a desired portion of donor tibia 505 may be selected for grafting based, at least in part, on the density profile determined from the image. In addition, information regarding any imaged soft tissue attachments may aid in planning placement of the soft tissue attachments with respect to the patient's anatomy.

Figure 4C:
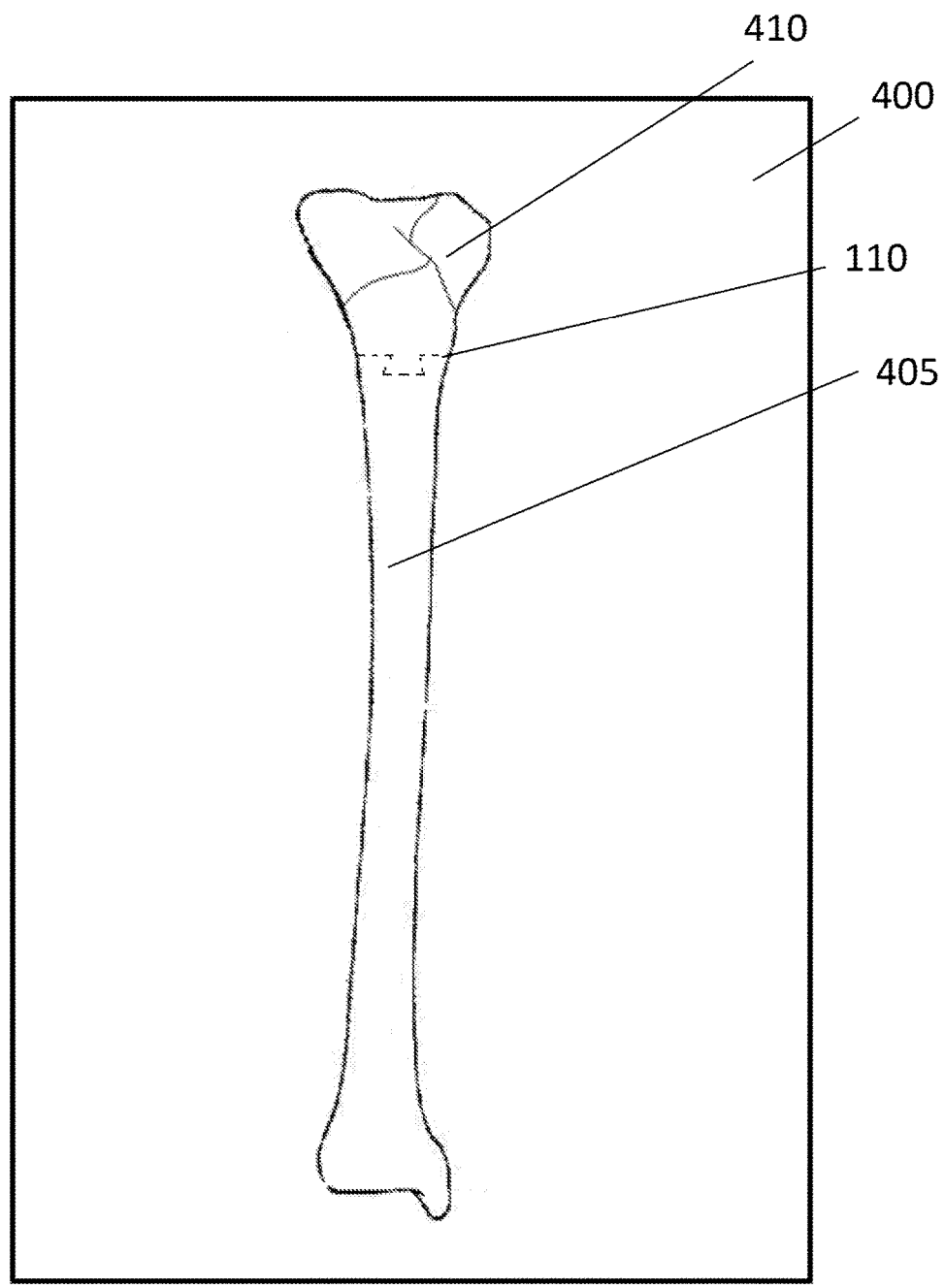
FIG. 4C illustrates an aspect of a surgical plan for the bone of FIG. 4A.
Figure 4D:
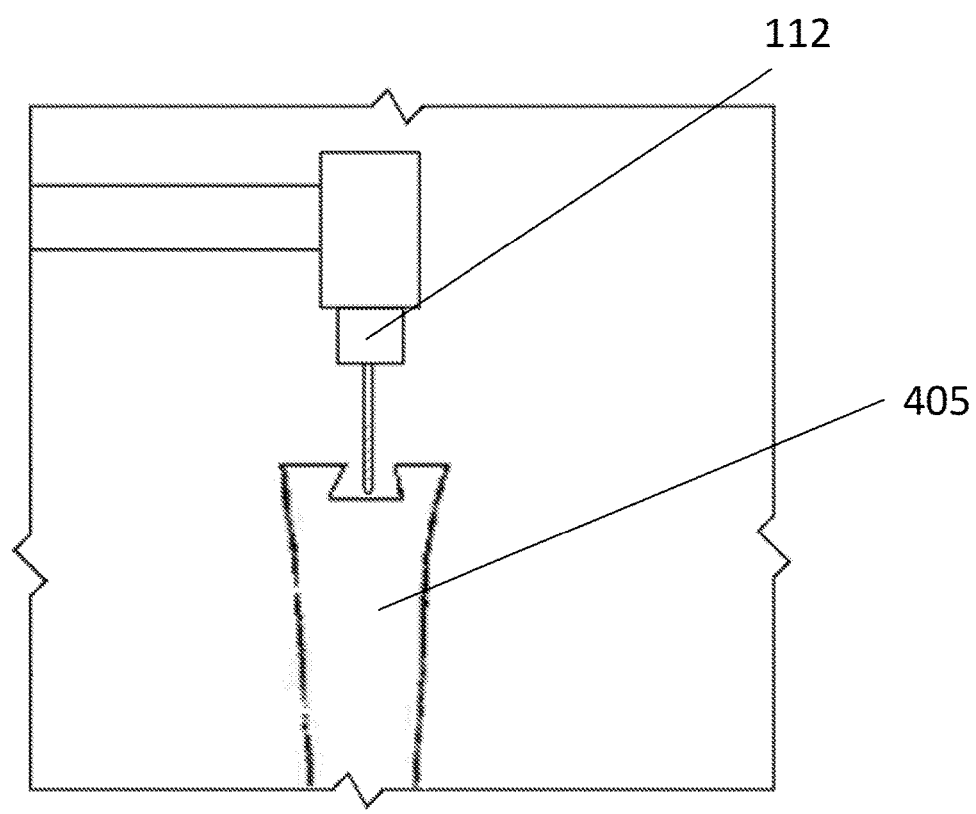
FIG. 4D is a highly schematic representation of the haptic device of FIG. 1 performing a resection on the bone of FIG. 4A.

Whether or not donor tibia 505 is imaged, the surgeon may use processor based system 36 to plan the surgical procedure on the patient's tibia 405, including the step 220 of defining the volume and/or geometry of the resection of the patient's tibia 405. Based on this determination, haptic object 110 may be defined in step 230. For example, as shown in FIG. 4C, haptic object 110 may take the form of a boundary line distal to the fracture site 410. Processor based system 36 may include a number of predefined geometries and/or volumes that may be utilized by the surgeon in defining the haptic object 110. For example, in the illustrated example, the haptic object 110 includes a dovetail shape that may provide a site with which the allograft may securely interlock.

The patient's tibia 405 is registered as described above in connection with step 240. A surgical tool 112, such as a drill, bur, or other resecting tool, may be coupled to haptic device 113 and used to resect tibia 405 according to the surgical plan. As described above, the haptic device 113 may autonomously or semi-autonomously guide the surgical tool 112 using the constraints of the haptic object 110 to remove the desired geometry and/or volume of bone, as shown in FIG. 4C. The path of the tip of the surgical tool 112 is tracked and information regarding the actual volume of bone removed is stored in computer 36 and/or computer 10. It is contemplated that the geometry and/or volume of tibia 405 removed would be extremely close or identical to the surgical plan, although deviations may be possible.

Figure 4E:
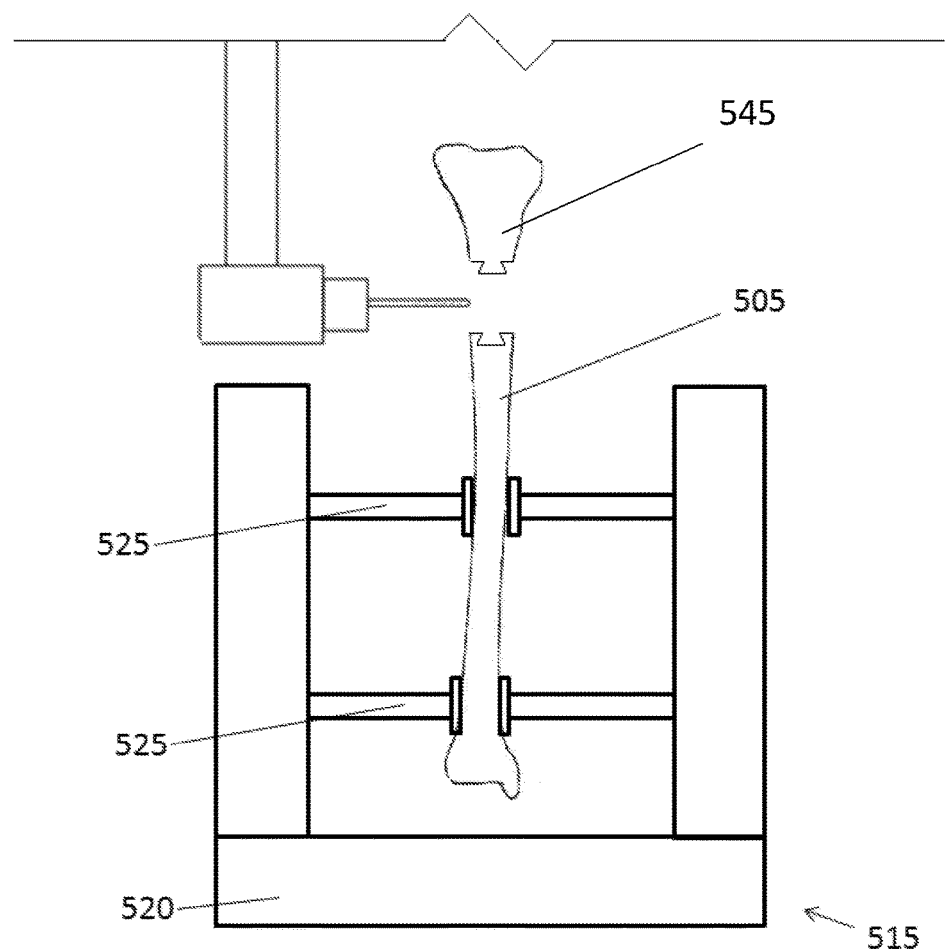
FIG. 4E is a highly schematic representation of the haptic device of FIG. 1 performing a resection on the donor bone of FIG. 4B.

As the haptic device 113 resects tibia 405, data is stored in computer 10 (and/or computer 36) to determine the geometry and/or volume of donor tibia 505 that needs to be removed, as provided in step 260, in order to provide a corresponding fit with the resected tibia 405. If not already performed, the donor tibia 505 is registered, for example in the same manner in which the patient's tibia 405 was registered. The registration takes place after donor tibia 505 is securely positioned in holding device 515 to help ensure that the global or real world coordinate system does not change with respect to the registered coordinate system, for example by unintentional movement of donor tibia 505 within holding device 515. It should be noted that the holding device 515 may also be registered during this step. Whether the registration is performed before or after the registration and resection of patient's tibia 405, the donor tibia 505 is resected using haptic device 113, as shown in FIG. 4E, so that the implantable portion 545 of donor tibia 505 has the desired shape as defined in step 260. As noted above, instead of or in addition to securing the donor tibia 405 in a holding device 515, tracking devices may be attached to the donor tibia 405 so that any movement of the donor tibia 405, intentional or otherwise, is tracked by the navigation system. With the donor tibia 505 resected, the surgeon may implant the implantable portion 545 onto the resected portion of the patient's tibia 405, in this case with a dovetail interlocking shape. Positioning of the implantable portion 545 or donor tibia 505 may be completed manually, or with the aid of haptic device 113, for example by using a clamp or other surgical tool 112 connected to haptic device 113 to hold and position the implantable portion 545 or donor tibia 505 onto the patient's resected tibia 405 with precision. If soft tissue, such as the patellar tendon, was kept intact on the implantable portion 545 of donor tibia 505, that tendon may be attached to the patient and the procedure completed. In other embodiments, repaired bone 505 with implantable portion 545 positioned thereon may be imaged and modeled. The obtained images and/or model of the repaired bone may be compared to previous models or surgical plans to determine whether a desired surgical result has been achieved. If additional changes to the repair bone are warranted, instructions may be sent to haptic device 113 to reorient implantable portion 545 on bone 505 or resect a portion of implantable portion 545 as required.

It should be understood that although a dovetail interlocking feature is described above, other features of aiding implantation may be used instead or in addition. For example, other types of geometric keys, including tongue and groove, may be correspondingly formed in the patient's tibia 405 and donor tibia 505. In fact, any corresponding geometries intended to mate with one another may be created. For example, corresponding geometries that provide for a press fit and/or interference fit may be created. Further, the donor bone may be resected into multiple pieces that fit together to form the desired implant shape. This type of procedure may be useful, for example, when a middle portion of a bone is being replaced, similar to the procedure described in connection with FIGS. 3A-E. Still further, if the donor bone is to be screwed to the patient's bone (or otherwise affixed with hardware), features to assist that fixation may be provided on the patient's bone and/or donor bone. For example, if a screw is to be used to screw the donor bone into the patient bone, threaded screw holes or pilot holes may be drilled into the donor bone by haptic device 113 to provide for improved screw fixation of the donor bone to the patient's bone. In addition to, or alternatively to, any of the features described above, haptic device 113 may be programmed to create channels in the patient's bone and/or the prosthesis so that bone cement or other adhesive may be placed within the one or more channels to facilitate fixation of the prosthesis to the bone.

Still further, in some procedures one or more pieces of hardware, such a bone plate, may be implanted to additionally secure other prosthetic devices, such as a donor bone or multiple pieces of donor bone. In some cases, a bone plate may be bent by the surgeon intraoperatively to provide the best fit between the plate and the anatomy. However, such bending is often done by trial and error. With the above disclosure in mind, if a surgeon bends a plate intraoperatively, the surgeon may probe the bone-contacting surface of the plate to determine the geometry of the surface, which may be compared by computer 10 and/or 36 to the surface geometry of the patient anatomy to determine whether or not, and to what extent, the contour of the bone plate matches the contour of the anatomy to which the bone plate will be affixed.

Although the bulk allograft procedure is described above in relation to a tibia 405, it should be understood that the procedure applies to other bones and to other types of resections. In addition, the procedure could be performed with the donor bone being a portion of the patient's own bone from another site. With such an autograft procedure, the steps outlined above would be generally similar, but with the haptic device 113 being used to resect the patient's host bone and also the patient's own donor bone which may come from another part of the patient's body.

It should further be clear that the imaging and registration of the patient's bone and donor bone may be performed essentially in any order. For example, the patient's bone may be imaged and registered, then resected, and then the donor bone registered and resected. Alternatively, the patient and donor bone may both be registered prior to performing resection of either bone.

In addition, although the procedure described in connection with FIGS. 4A-E uses a donor tibia 505 as a prosthesis, other prostheses, including metal and/or plastic prostheses, may be used to replace the resected portion of the patient's tibia 405. For example, metal and/or plastic blank may be secured in holding device 515, with haptic device 113 shaping the metal and/or plastic blank prosthesis to the desired shape prior to implantation. Similarly, some groups of prostheses have similar or identical features to other groups of prostheses, with one group also having additional features. For example, some knee implants have posts for helping secure the implant to the bone, with other implants having similar or identical features except the post is omitted. With such groups of prostheses, the type of prosthesis with the extra feature may be stocked and secured in the holding device 515. If the surgeon desires to use the implant with the additional feature, it may be otherwise shaped based on the data obtained during bone removal. If the surgeon desires to use the implant but remove the additional feature (such as the post), the post may additionally be removed through machining by haptic device 113. This may reduce the number of types of prostheses required to be stocked prior to a surgical procedure. The above concepts are also applicable to the procedure described in connection with FIGS. 3A-E, for example by shaping a porous metallic structure to replace the bone removed, with the void filler and/or bone growth composition being added to the metallic structure to complete the implantation.

Still further, although certain steps are described as being performed on processor based system 36 and/or computer 10, it should be understood that such steps may be performed on a separate computer device with the results imported to processor based system 36 and/or computer 10. For example, the surgical plan may be created on a separate computer device prior to the surgery and the results of such plan imported to processor based system 36 for use during the surgery.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, features described in relation to one embodiment may be combined with features described in relation to another embodiment.

The invention claimed is:

1. A method of performing a surgical procedure on a patient, comprising:
   planning a resection of a bone of the patient;
   removing a volume of the bone with a surgical tool according to the planned resection;
   tracking data corresponding to a shape and volume of the removed bone with a computer system operatively coupled to the surgical tool; and
   implanting a prosthesis onto the bone of the patient based on the tracked data corresponding to the shape and volume of the removed bone;
   wherein the implanted prosthesis is deposited on the bone with a deposition tool operatively coupled to a robotic device during the implanting step.

2. The method of claim 1, wherein the surgical tool for removing the volume of the bone is operatively coupled to a robotic device during the removal step.

3. The method of claim 1, wherein the surgical tool is a manual tool.

4. The method of claim 1, wherein the deposition tool is a syringe device.

5. The method of claim 1, wherein the implanted prosthesis is an ultraviolet curable resin.

6. The method of claim 1, further comprising monitoring a temperature of the prosthesis during the implanting step.

7. The method of claim 1, wherein the deposition tool includes a first deposition tool and a second deposition tool, the prosthesis includes a first prosthesis and a second prosthesis, and wherein the implanting step further comprises:
   forming a lattice on the resected bone with the first deposition tool containing the first prosthesis therein, the first deposition tool operatively coupled to the robotic device; and
   filling the lattice with the second prosthesis contained in the second deposition tool operatively coupled to the robotic device.

8. The method of claim 1, wherein the deposition tool includes a first deposition tool and a second deposition tool, the prosthesis includes a first prosthesis layer and a second prosthesis layer, and wherein the implanting step further comprises:
implanting the first prosthesis layer on the resected bone with the first deposition tool operatively coupled to the robotic device, the first prosthesis layer having a first density; and
after implanting the first prosthesis layer, implanting the second prosthesis layer on the first prosthesis layer with the second deposition tool operatively coupled to the robotic device, the second prosthesis layer having a second density different than the first density.

9. The method of claim 8, wherein the second density is greater than the first density.

10. The method of claim 1, further comprising shaping the prosthesis using the surgical tool so that the prosthesis has a shape complementary to the shape of the removed bone.

11. The method of claim 10, wherein the surgical tool is selected from one of the group consisting of a bur, saw, laser, cautery device, and waterjet.

12. The method of claim 10, wherein, during the step of shaping the prosthesis, the prosthesis is secured to a holding device.

13. The method of claim 10, wherein the step of removing the volume of the bone includes forming a first geometric shape in the bone and the step of shaping the prosthesis includes forming a second geometric shape in the prosthesis, the first geometric shape being keyed to the second geometric shape.

14. The method of claim 13, wherein the first and second geometric shapes form a dovetail configuration.

15. The method of claim 10, wherein the step of implanting the prosthesis onto the bone of the patient includes coupling the prosthesis onto the bone with a fastener.

16. The method of claim 15, wherein the fastener is selected from the group consisting of bone screws and bone pins.

17. The method of claim 16, further comprising forming a feature for accepting the fastener into at least one of the bone and the prosthesis.

18. The method of claim 17, wherein the feature is selected from one of the group consisting of a threaded screw hole and pilot hole.

19. The method of claim 10, wherein the step of shaping the prosthesis using the surgical tool includes forming a plurality of discrete prostheses, and wherein the step of implanting the prosthesis onto the bone includes implanting each of the discrete prostheses.

* * * * *